United States Patent
Kim et al.

(10) Patent No.: US 8,952,060 B2
(45) Date of Patent: Feb. 10, 2015

(54) COMPOSITION FOR PREVENTING HAIR LOSS OR FOR STIMULATING HAIR GROWTH

(75) Inventors: Hyoung-Jun Kim, Yongin-si (KR); Won Seok Park, Seoul (KR); Hyun Ju Koh, Anyang-si (KR); Pil Joon Park, Yongin-si (KR); Su Na Kim, Yongin-si (KR); Kang-Yell Choi, Seoul (KR); Ju-Yong Yoon, Seoul (KR); Soung-Hoon Lee, Asan-si (KR)

(73) Assignee: Amorepacific Corporation, Seoul (KR)

( * ) Notice: Subject to any disclaimer, the term of this patent is extended or adjusted under 35 U.S.C. 154(b) by 509 days.

(21) Appl. No.: 13/319,483

(22) PCT Filed: May 11, 2010

(86) PCT No.: PCT/KR2010/002982
§ 371 (c)(1),
(2), (4) Date: Nov. 8, 2011

(87) PCT Pub. No.: WO2010/131887
PCT Pub. Date: Nov. 18, 2010

(65) Prior Publication Data
US 2012/0065262 A1    Mar. 15, 2012

(30) Foreign Application Priority Data
May 12, 2009 (KR) .................. 10-2009-0041442

(51) Int. Cl.
*A61K 31/19* (2006.01)
*A23L 1/30* (2006.01)
*A61K 8/36* (2006.01)
*A61Q 7/00* (2006.01)

(52) U.S. Cl.
CPC . *A61K 31/19* (2013.01); *A23L 1/30* (2013.01); *A23V 2002/00* (2013.01); *A61K 8/361* (2013.01); *A61Q 7/00* (2013.01)
USPC ........................................................ 514/557

(58) Field of Classification Search
CPC .................................................... A61K 31/19
USPC ........................................................ 514/557
See application file for complete search history.

(56) References Cited

U.S. PATENT DOCUMENTS

| 6,316,022 | B1* | 11/2001 | Mantelle et al. ............... 424/448 |
| 8,088,787 | B2* | 1/2012 | Hong et al. .................... 514/282 |
| 2001/0005512 | A1 | 6/2001 | Anderson |
| 2006/0223888 | A1 | 10/2006 | Abbott et al. |
| 2007/0207950 | A1 | 9/2007 | Yao et al. |

FOREIGN PATENT DOCUMENTS

| CN | 101081272 A | 12/2007 |
| JP | 2007-530487 A | 11/2007 |
| WO | WO 03/063810 A2 | 8/2003 |
| WO | WO 2005/092283 A1 | 10/2005 |
| WO | WO 2007/095584 A2 | 8/2007 |

OTHER PUBLICATIONS

Kostrouchova, M. et al., "Valproic Acid, a Molecular Lead to Multiple Regulatory Pathways", Folia Biologica (Praha), 2007, pp. 37-49, 53.
Byoung-San Moon, et al., Bone Morphogenetic Protein 4 Stimulates Neuronal Differentiation of Neuronal Stem Cells Through the ERK Pathway: Experimental and Molecular Medicine, vol. 41, pp. 116-125, 2009.
Kyung-Cheol Sohn, et al., "Pita, a β-catenin-regulated Transcription Factor, Regulated the Differentiation of Outer Root Sheath Cells Cultured in Vitro", Journal of Dermatological Science, vol. 54, pp. 6-11, 2009.
"The Medical History", No. 219, vol. 2, Ishiyaku Publishing Co., Oct. 14, 2006, pp. 163- 164.
"The Medical History", No. 219, vol. 1, Ishiyaku Publishing Co., Jul. 7, 2002, pp. 65-69.
Iranian Journal of Pharmacology & Therapeutics (2005), 4(2), 143-145.
Japan Clinical studies (separated volume), area by syndrome, No. 38 psychiatric syndrome, Japan Clinical studies Inc., 2003, Jun. 28, P362-365.

* cited by examiner

*Primary Examiner* — Raymond Henley, III
(74) *Attorney, Agent, or Firm* — Dickstein Shapiro LLP

(57) ABSTRACT

Provided is a composition for preventing hair loss or promoting hair growth including valproic acid or a pharmaceutically acceptable salt thereof as an active ingredient. The composition may be applied to various industrial fields, including pharmaceutical, cosmetic and beauty aid industries.

9 Claims, 5 Drawing Sheets

Control (DW, MC 1%, Tween 80 0.5%)
VPA: Sodium Valproate

Control (PG:ethanol:DW=5:3:2)
VPA: Sodium Valproate,
**p<0.01 vs Control

COMPOSITION FOR PREVENTING HAIR LOSS OR FOR STIMULATING HAIR GROWTH

TECHNICAL FIELD

The present disclosure relates to a composition for inhibiting hair loss and promoting hair growth.

BACKGROUND ART

In general, hair loss occurs naturally or is promoted chemically through the use of a specific therapeutic agent designed to alleviate some medical conditions, such as cancers. Such hair loss is followed by a lack of hair regrowth leading to partial or total baldness.

Recently, mans suffering from alopecia have increased due to environmental pollution, stress, diet, fatigue, improper eating habits, or the like. Under these circumstances, increased attention has been given to agents for improving alopecia conditions. The present inventors also have conducted many studies to develop an agent for inhibiting hair loss and promoting hair growth.

DISCLOSURE

Technical Problem

The present disclosure is directed to providing a composition for inhibiting hair loss and promoting hair growth.

The present disclosure is also directed to providing a pharmaceutical composition including a composition for inhibiting hair loss and promoting hair growth.

The present disclosure is also directed to providing a cosmetic composition including a composition for inhibiting hair loss and promoting hair growth.

Technical Solution

In one aspect, there is provided a composition for inhibiting hair loss and promoting hair growth, containing valproic acid or a pharmaceutically acceptable salt thereof as an active ingredient.

In another aspect, there is provided a pharmaceutical composition including a composition for inhibiting hair loss and promoting hair growth, containing valproic acid or a pharmaceutically acceptable salt thereof as an active ingredient.

In still another aspect, there is provided a cosmetic composition including a composition for inhibiting hair loss and promoting hair growth, containing valproic acid or a pharmaceutically acceptable salt thereof as an active ingredient.

Advantageous Effects

The composition disclosed herein includes valproic acid or a pharmaceutically acceptable salt thereof as an active ingredient, and is effective for preventing hair loss and promoting hair growth.

BEST MODE

Figure 1:
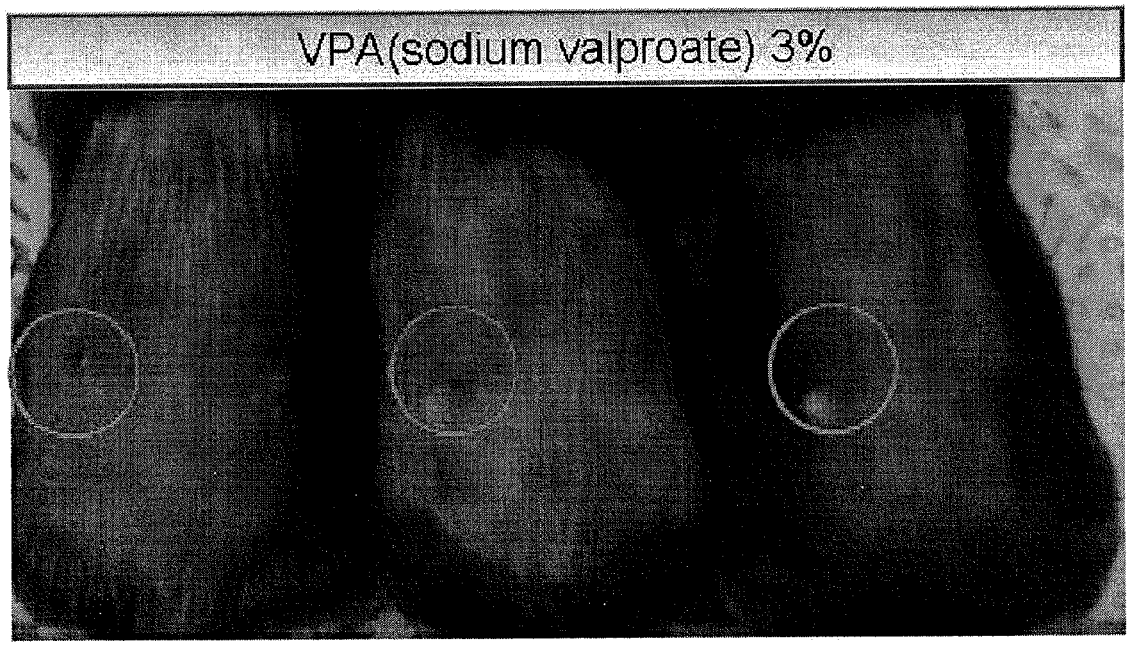
FIG. 1 is a photograph showing the progress of hair growth after sub-cutaneous injection of sodium valproate according to one embodiment.

As used herein, the term 'hair loss' means elimination of hair from scalps or loosening or thinning of hair. The expression 'preventing hair loss' means preventing and inhibiting such hair loss, and the expression 'promoting hair growth' means promoting formation of new hair or keeping the existing hair growing healthily.

As used herein, unless otherwise specified, it is to be understood that the expression 'compound as an active ingredient' includes not only a compound in a free form (free acid or free base) but also a prodrug, polymorph, hydrate, solvate, tautomer, stereoisomer, pharmaceutically acceptable salt thereof and any active form thereof. In addition, the term includes a suitable metabolic product of the corresponding compound (any suitable form).

As used herein, the expression 'pharmaceutically acceptable dose' means a dose applied generally in drug administration, wherein such a dose prevents hair loss and promotes hair growth at the active site of a subject without any significant toxicity, irritation or allergic conditions.

Valproic acid (2-propylpentanoic acid) used as an active ingredient of the composition according to one embodiment has been used as an anticovulsant agent in treating epilepsy, and sometimes as a mood stabilizer in the case of bipolar disorders. It is known that valproic acid induces various cellular reactions. However, mechanisms of valproic acid that alleviates convulsions and inhibits abnormal behaviors have not been clearly shown to date. Moreover, it is reported that administration of valproic acid may cause hair loss as a side effect.

It is now demonstrated that valproic acid or a pharmaceutically acceptable salt thereof is significantly effective for preventing hair loss and promoting hair growth. Thus, in one aspect, there is provided a composition containing valproic acid or a pharmaceutically acceptable salt thereof as an active ingredient. There is no particular limitation in valproic acid or a pharmaceutically acceptable salt thereof, as long as it does not adversely affect prevention of hair loss and promotion of hair growth. For example, the salt may be sodium valproate. Valproic acid or a pharmaceutically acceptable salt thereof functions as a GSK-3β inhibitor, stabilizes β-catenin in hair stem cells and controls differentiation and growth of cells accordingly, thereby promoting hair growth.

According to one embodiment, the composition is formulated for transdermal administration, and more particularly, provided as a formulation for subcutaneous injection or skin application. We have conducted tests by introducing the active ingredient via various routes, including subcutaneous injection, intravenous injection, oral administration or skin application. As a result, it is shown that when the active ingredient is administered via subcutaneous injection or skin application, it provides an excellent effect of preventing hair loss and promoting hair growth. For example, oral administration of valproic acid inhibits hair growth to the contrary. However, transdermal administration (subcutaneous injection or skin application) of valproic acid promotes hair growth.

The composition according to one embodiment may include valproic acid or a pharmaceutically acceptable salt thereof in an amount of 0.5-30 wt %, particularly 2.0-25 wt %, based on the total weight of the composition. When valproic acid or a pharmaceutically acceptable salt thereof is used in the above-defined range, it shows an excellent effect of inhibiting hair loss and promoting hair growth without any side effects. When the active ingredient is used in an amount lower than the above-defined range, it is not possible to expect a sufficient effect of inhibiting hair loss and promoting hair growth. On the other hand, when the active ingredient is used in an amount greater than the above-defined range, undesired side effects or degradation of formulation stability may occur.

According to one embodiment, the composition may be provided as a formulation for local drug administration to a specific site. The composition for preventing hair loss and promoting hair growth may be provided as a local use formulation for preventing hair loss and promoting hair growth using a local drug delivery system capable of local drug administration to a specific site. The local drug delivery system is developed in order to realize a maximized effect at a desired site by using a small amount of drug, and has advantages in that it maintains a high local concentration and avoids side effects caused by systemic administration. Various kinds of biocompatible polymers may be used in the local drug delivery system. The composition disclosed herein may be provided as a subcutaneous injection formulation for local administration. In addition, the composition may be formulated into a patch, pad, gel or ointment for use in a specific site.

In general, hair growth occurs during activity cycles including a crossing of a growing stage with a resting stage and the activity cycle may be divided into the three stages of a growing stage, a regressing stage and a resting stage. The growing stage may be characterized by rapid proliferation of cells and deep penetration of hair follicles into the skin, and thus is different from hair formation. The growing stage is followed by the regressing stage, which is a transition period characterized by cessation of cell division. During the regressing stage, hair follicles regress through the skin and hair growth is stopped. The regressing stage is followed by the resting stage, in which the regressing hair follicles include germs having densely packed dermal papilla cells. Initiation of a new growing stage from the resting stage is induced by rapid cell proliferation, expansion of dermal papilla and synthesis of basal membrane elements in the germs.

Therefore, it is required to prevent hair loss (to prevent depilation) or to induce regrowth of hair (to promote hair growth) by stimulating or extending the growing stage. The composition according to one embodiment shows at least one effect selected from an effect of preventing loss of the existing hair, an effect of improving the condition of hair (for example, thickening the exiting hair), and an effect of forming new hair. In addition, the composition disclosed herein is capable of activating dermal papilla cells, thereby inducing hair growth.

In another aspect, there is provided a pharmaceutical composition including a composition containing valproic acid or a pharmaceutically acceptable salt thereof. Such a pharmaceutical composition may further include pharmaceutical adjuvants, such as preservatives, stabilizers, hydrating agents or emulsifying accelerants, salts for controlling osmotic pressure and/or buffering agents, and other therapeutically useful materials, and may be formulated into various forms for parenteral administration in a manner generally known to those skilled in the art.

Particular examples of the forms for parenteral administration include injection formulations, drops, ointment, lotion, gel, cream, spray, suspension, emulsion, suppository, patches, etc., but are not limited thereto.

The pharmaceutical composition according to one embodiment may be administered via a parenteral, rectal, local, transdermal, subcutaneous route, or the like. For example, the pharmaceutical composition according to one embodiment may be administered locally to scalps.

In addition, the pharmaceutically acceptable dose of the active ingredient (i.e. administration dose) may be varied with various factors, including the age, sex and body weight of a subject to be treated, particular type of disease to be treated, pathological condition, severity of disease or pathological condition, administration route and judge of a medical professional. The administration dose may be determined easily by those skilled in the art based on the above-mentioned factors. In general, the active ingredient may be administered in a dose between 0.01 mg/kg/day and 1000 mg/kg/day, particularly between 1 mg/kg/day and 40 mg/kg/day, but the scope of the present disclosure is not limited thereto. For example, when applying a formulation for external skin application to the skin, 1 mL of the formulation may be administered twice per day for adults. In addition, in the case of a formulation for local subcutaneous injection, 1 mL of the formulation may be administered as a unit dose every other week. The concentration of the active ingredient may be controlled in a range of 0.5-30%, particularly 2-25%.

In still another aspect, there is provided a cosmetic composition including a composition containing valproic acid or a pharmaceutically acceptable salt thereof. The cosmetic composition may further include adjuvants currently used in the field of cosmetics and dermatology. Such adjuvants may include fat, organic solvents, dissolving agents, concentrating agents, gelling agents, softeners, anti-oxidants, suspending agents, stabilizers, foaming agents, fragrances, surfactants, water, ionic or non-ionic emulsifiers, fillers, metal ion blockers, chelating agents, preservatives, vitamins, blocking agents, wetting agents, essential oil, dyes, pigments, hydrophilic or oleophilic activating agents, lipid vesicles or other ingredients currently used in cosmetic products. Such adjuvants may be used in an amount currently used in the field of cosmetics and dermatology.

The cosmetic composition may be a beauty aid composition including a cosmetically or dermatologically acceptable medium or base. Such compositions include any formulations suitable for local applications, such as solution, gel, solid, anhydrous paste products, oil in water emulsion, suspension, microemulsion, microcapsules, microgranules or ionic (liposome) and non-ionic vesicular dispersion. In a variant, such compositions may be provided in the form of cream, skin, lotion, powder, ointment, spray or conceal stick. Such compositions may be obtained in a manner generally known to those skilled in the art. Further, the composition disclosed herein may be used in the form of foam or an aerosol composition further including a pressurized propellant.

The cosmetic composition including valproic acid or a pharmaceutically acceptable salt thereof may be formulated into any forms with no particular limitation. For example, the cosmetic composition may be formulated into various forms of cosmetics, including skin softener, astringent, skin tonic agent, nutrient cream, massage cream, essence, eye cream, eye essence, cleansing cream, cleansing foam, cleansing water, pack, powder, body lotion, body cream, body oil and body essence.

The cosmetic composition may be provided for skin application or for absorption into skin by using microneedles, etc.

MODE FOR INVENTION

The examples (and experiments) will now be described. The following examples (and experiments) are for illustrative purposes only and not intended to limit the scope of the present disclosure.

EXAMPLE 1

According to one embodiment, sodium valproate (VPA) is administered to subjects via subcutaneous injection and then tested for its effect for promoting hair growth.

Seven week aged female mice (C57BL/6) are subjected to depilation at their back portions. Next, 3% sodium valproate solution is administered via subcutaneous injection to the left side of each depilated back portion in a unit dose of 50 µL at an interval of 3-4 days seven times in total. Then, the degree of hair growth is observed 1, 16 and 30 days after starting the test. The results are shown in FIG. 1.

In the test of FIG. 1, sodium valproate is injected subcutaneously to the left portion (marked by a circle) of the back of each mouse. After 16 days, it is shown that hair growth is promoted as compared to the control (right side of the back of each mouse). After 30 days, it is shown that new hair follicles are formed.

EXAMPLE 2

According to one embodiment, sodium valproate is administered orally to subjects and then tested for its effect for promoting hair growth.

Seven week aged female mice (C57BL/6) are subjected to depilation at their back portions. Next, valproic acid is administered orally to mice of each test group everyday for 5 weeks. The control (mixed solution of distilled water, 1% methyl cellulose and 0.5% Tween 80™) and sodium valproate each are administered in a unit dose of 0.2 g/kg.

After the administration, hair growth is observed at an interval of one week. After 5 weeks, hair weight after the depilation is measured. The results of hair growth are shown in FIG. 2, and those of hair weight measurement are shown in FIG. 3.

Figure 2:
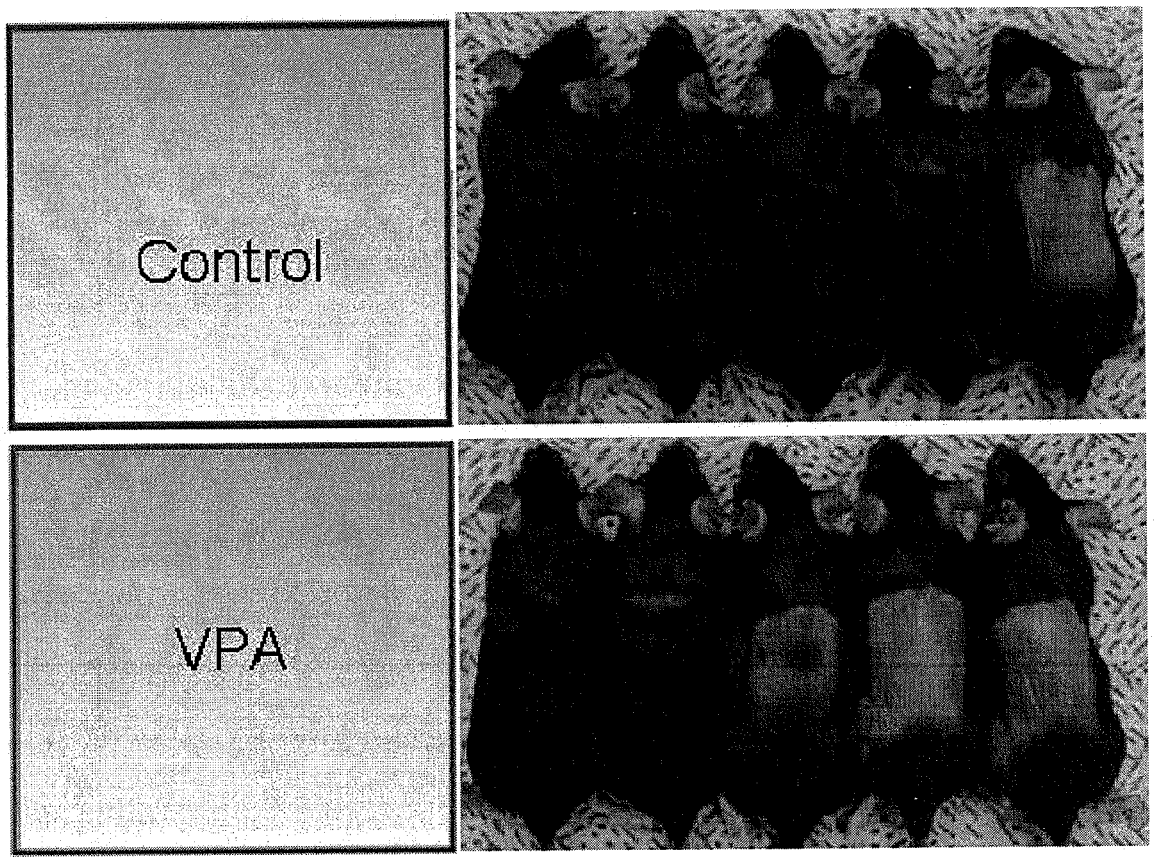
FIG. 2 is a photograph showing the progress of hair growth after oral administration of sodium valproate.
Figure 3:
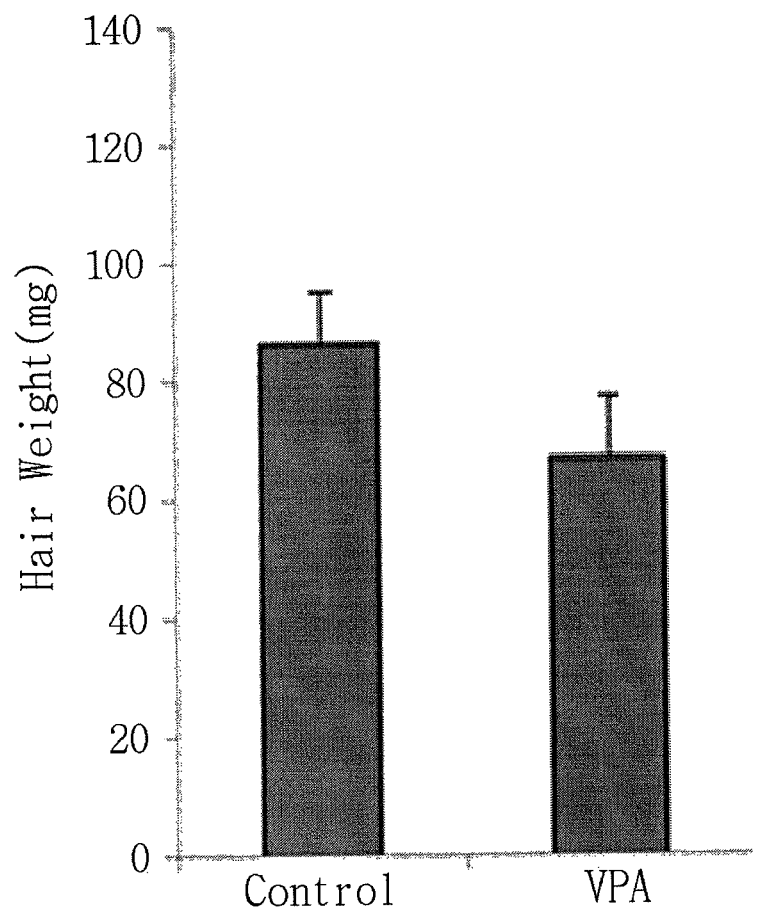
FIG. 3 is a photograph showing the result of measuring hair weight 6 weeks after oral administration of sodium valproate.

As can be seen from FIG. 2, oral administration of sodium valproate delays hair growth as compared to the control. As can be seen from FIG. 3, the control shows a hair weight of about 85 mg, while the hair weight of the sodium valproate treating group is merely 65 mg. Thus, it can be seen from the results of FIG. 2 and FIG. 3 that oral administration of sodium valproate significantly delays hair growth.

EXAMPLE 3

According to one embodiment, sodium valproate is administered to subjects via external application to the skin and then tested for its effect for promoting hair growth.

Seven week aged female mice (C57BL/6) are subjected to depilation at their back portions. Next, 7.2% sodium valproate is applied to the depilated back portions of mice of each test group twice per day. As a control, a mixed solution of propylene glycol/ethanol/water (5:3:2) is used.

After the skin application, hair growth is observed at an interval of one week. After 6 weeks, hair weight after the depilation is measured. The results of hair growth are shown in FIG. 4, and those of hair weight measurement are shown in FIG. 5.

Figure 4:
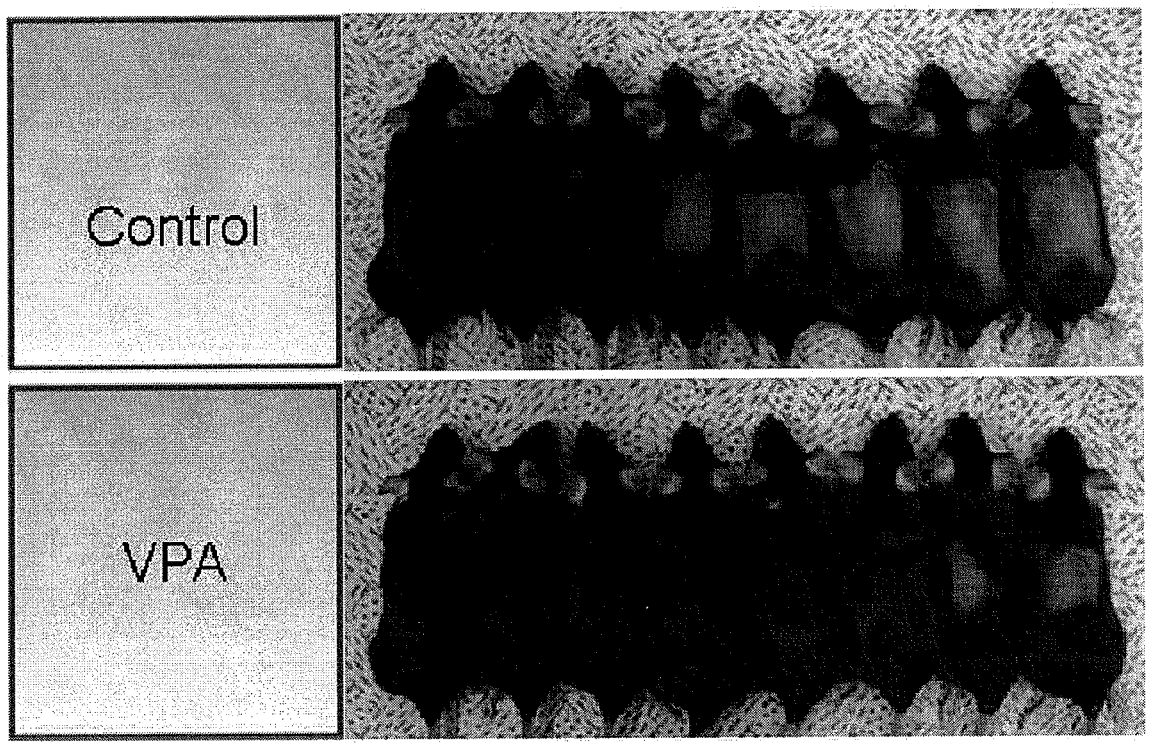
FIG. 4 is a photograph showing the progress of hair growth after skin application of sodium valproate.
Figure 5:
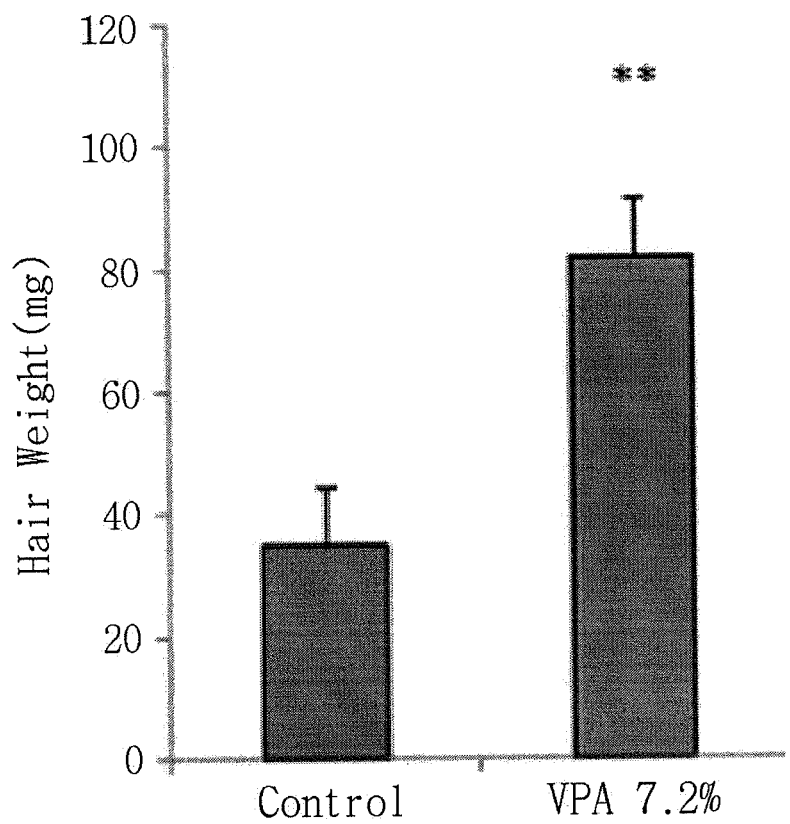
FIG. 5 is a photograph showing the result of measuring hair weight 6 weeks after skin application of sodium valproate.

As can be seen from FIG. 4, skin application of sodium valproate promotes hair growth as compared to the control. As can be seen from FIG. 5, the control shows a hair weight of about 35 mg, while the hair weight of the sodium valproate treating group is 80 mg or more. Thus, it can be seen from the results of FIG. 4 and FIG. 5 that skin application of sodium valproate significantly promotes hair growth.

Hereinafter, non-limiting formulation examples of the composition disclosed herein will be described. However, various types of formulations other than those described hereinafter may be provided and the following formulation examples are illustrative purposes only.

FORMULATION EXAMPLE 1

Ointment for Skin Application

Ointment is prepared by using the composition as shown in the following Table 1 in a manner generally known to those skilled in the art.

TABLE 1

| Ingredients | Amount (wt %) |
|---|---|
| Valproic acid | 0.1 |
| Glycerin | 8.0 |
| Butylene glycol | 4.0 |
| Liquid paraffin | 15.0 |
| Beta-glucan | 7.0 |
| Carbomer | 0.1 |
| Caprylic/Capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, pigment, fragrance | q.s. |
| Purified water | balance |

FORMULATION EXAMPLE 2

Preparation of Injection Formulation

An injection formulation is prepared by using the composition per ample (2 mL) as shown in the following Table 2 in a manner generally known to those skilled in the art.

TABLE 2

| Ingredients | Amount (wt %) |
|---|---|
| Valproic acid | 10.0 |
| pH modifier | q.s. |
| Sterilized distilled water for injection | q.s. |

FORMULATION EXAMPLE 3

Skin Softener (Skin Lotion)

Skin softener is prepared by using the composition as shown in the following Table 3 in a manner generally known to those skilled in the art.

TABLE 3

| Ingredients | Amount (wt %) |
|---|---|
| Valproic acid | 0.1 |
| Glycerin | 3.0 |
| Butylene glycol | 2.0 |

TABLE 3-continued

| Ingredients | Amount (wt %) |
| --- | --- |
| Propylene glycol | 2.0 |
| Carboxyvinyl polymer | 0.1 |
| PEG-12 nonylphenyl ether | 0.2 |
| Polysorbate 80 | 0.4 |
| Ethanol | 10.0 |
| Triethanol amine | 0.1 |
| Preservative, pigment, fragrance | q.s. |
| Purified water | Balance |

FORMULATION EXAMPLE 4

Skin Tonic Agent (Milk Lotion)

A skin tonic agent is prepared by using the composition as shown in the following Table 4 in a manner generally known to those skilled in the art.

TABLE 4

| Ingredients | Amount (wt %) |
| --- | --- |
| Valproic acid | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/Capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment, fragrance | q.s. |
| Purified water | Balance |

FORMULATION EXAMPLE 5

Nutrient Cream

Nutrient cream is prepared by using the composition as shown in the following Table 5 in a manner generally known to those skilled in the art.

TABLE 5

| Ingredients | Amount (wt %) |
| --- | --- |
| Valproic acid | 0.1 |
| Glycerin | 3.0 |
| Butylene glycol | 3.0 |
| Liquid paraffin | 7.0 |
| Beta-glucan | 7.0 |
| Carbomer | 0.1 |
| Caprylic/Capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, pigment, fragrance | q.s. |
| Purified water | Balance |

FORMULATION EXAMPLE 6

Massage Cream

Massage cream is prepared by using the composition as shown in the following Table 6 in a manner generally known to those skilled in the art.

TABLE 6

| Ingredients | Amount (wt %) |
| --- | --- |
| Valproic acid | 0.1 |
| Glycerin | 8.0 |
| Butylene glycol | 4.0 |
| Liquid paraffin | 45.0 |
| Beta-glucan | 7.0 |
| Carbomer | 0.1 |
| Caprylic/Capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Preservative, pigment, fragrance | q.s. |
| Purified water | Balance |

FORMULATION EXAMPLE 7

Pack

A pack is prepared by using the composition as shown in the following Table 7 in a manner generally known to those skilled in the art.

TABLE 7

| Ingredients | Amount (wt %) |
| --- | --- |
| Valproic acid | 0.1 |
| Glycerin | 4.0 |
| Polyvinyl alcohol | 15.0 |
| Hyaluronic acid extract | 5.0 |
| Beta-glucan | 7.0 |
| Allantoin | 0.1 |
| Nonylphenyl ether | 0.4 |
| Polysorbate 60 | 1.2 |
| Ethanol | 6.0 |
| Preservative, pigment, fragrance | q.s. |
| Purified water | balance |

INDUSTRIAL APPLICABILITY

The composition disclosed herein includes valproic acid or a pharmaceutically acceptable salt thereof as an active ingredient, and is effective for preventing hair loss and promoting hair growth. Therefore, the composition may be applied to various industrial fields, including pharmaceutical, cosmetic and beauty aid industries.

The invention claimed is:

1. A method for inhibiting hair loss or promoting hair growth comprising administering an effective amount of a composition comprising valproic acid or a pharmaceutically acceptable salt thereof as an active ingredient to a subject in such need.

2. The method for inhibiting hair loss or promoting hair growth according to claim 1, wherein the valproic acid or a pharmaceutically acceptable salt thereof is sodium valproate.

3. The method for inhibiting hair loss or promoting hair growth according to claim 1, wherein the valproic acid or a pharmaceutically acceptable salt thereof is present in an amount of 0.5-30 wt % based on the total weight of the composition.

4. The method for inhibiting hair loss or promoting hair growth according to claim 3, wherein the valproic acid or a pharmaceutically acceptable salt thereof is present in an amount of 2.0-25 wt % based on the total weight of the composition.

5. The method for inhibiting hair loss or promoting hair growth according to claim 1, wherein the composition is transdermally administered to the subject.

6. The method for inhibiting hair loss or promoting hair growth according to claim 1, wherein the composition is subcutaneously injected to the subject or externally applied to the skin of the subject.

7. The method for inhibiting hair loss or promoting hair growth according to claim 1, wherein the composition is locally administered to deliver a drug to a specific site of the subject.

8. The method for inhibiting hair loss or promoting hair growth according to claim 1, wherein the composition is a pharmaceutical composition.

9. The method for inhibiting hair loss or promoting hair growth according to claim 1, wherein the composition is a cosmetic composition.

* * * * *